United States Patent
Dott et al.

(10) Patent No.: US 10,538,536 B2
(45) Date of Patent: Jan. 21, 2020

(54) PROCESS FOR THE PREPARATION OF 2-PYRAZOLO[1,5-A]PYRAZIN-2-YLPYRIDO[1,2-A]PYRIMIDIN-4-ONE COMPOUNDS

(71) Applicant: Hoffmann-La Roche Inc., Little Falls, NJ (US)

(72) Inventors: Pascal Dott, Basel (CH); Fabian Feyen, Basel (CH); Stefan Hildbrand, Basel (CH); Ursula Hoffmann, Basel (CH); Fabienne Hoffmann-Emery, Basel (CH); Roland Meier, Basel (CH); Gerard Moine, Basel (CH); Pankaj Rege, Basel (CH); Georg Wuitschik, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/171,936

(22) Filed: Oct. 26, 2018

(65) Prior Publication Data

US 2019/0144468 A1     May 16, 2019

Related U.S. Application Data

(63) Continuation of application No. PCT/EP2017/059714, filed on Apr. 25, 2017.

(30) Foreign Application Priority Data

Apr. 28, 2016  (EP) ..................... 16167494

(51) Int. Cl.
  *C07D 519/00*     (2006.01)
  *C07D 401/04*     (2006.01)
  *C07D 487/04*     (2006.01)

(52) U.S. Cl.
  CPC ......... *C07D 519/00* (2013.01); *C07D 401/04* (2013.01); *C07D 487/04* (2013.01); *C07B 2200/13* (2013.01)

(58) Field of Classification Search
  CPC .................................................. C07D 519/00
  See application file for complete search history.

(56) References Cited

FOREIGN PATENT DOCUMENTS

| EP | 2 773 638 B1 | 10/2015 |
|----|---|---|
| WO | 2011/089400 A1 | 7/2011 |
| WO | 2013/045516 A1 | 4/2013 |
| WO | 2013/067274 A1 | 5/2013 |
| WO | 2013/119916 A2 | 8/2013 |

OTHER PUBLICATIONS

ISR and Written Opinion of PCT/EP2017/059714 (Date of actual completion May 19, 2017).

*Primary Examiner* — Bruck Kifle
(74) *Attorney, Agent, or Firm* — Mark D. Kafka

(57) ABSTRACT

The present invention relates to a process for the preparation of 2-pyrazolo[1,5-a]pyrazin-2-ylpyrido[1,2-a]pyrimidin-4-one derivatives useful as pharmaceutically active compounds.

19 Claims, 2 Drawing Sheets

PROCESS FOR THE PREPARATION OF 2-PYRAZOLO[1,5-A]PYRAZIN-2-YLPYRIDO[1,2-A]PYRIMIDIN-4-ONE COMPOUNDS

CROSS-REFERENCE TO RELATED APPLICATIONS

This application is a continuation of, and claims priority to, International Patent Application No. PCT/EP2017/059714, filed on Apr. 25, 2017. This application also claims priority to European Patent Application No. 16167494.0, filed on Apr. 28, 2016. The entire contents of each of the above patent applications are hereby incorporated by reference.

The present invention relates to a process for the preparation of 2-pyrazolo[1,5-a]pyrazin-2-ylpyrido[1,2-a]pyrimidin-4-one derivatives useful as pharmaceutically active compounds.

Figure 1:
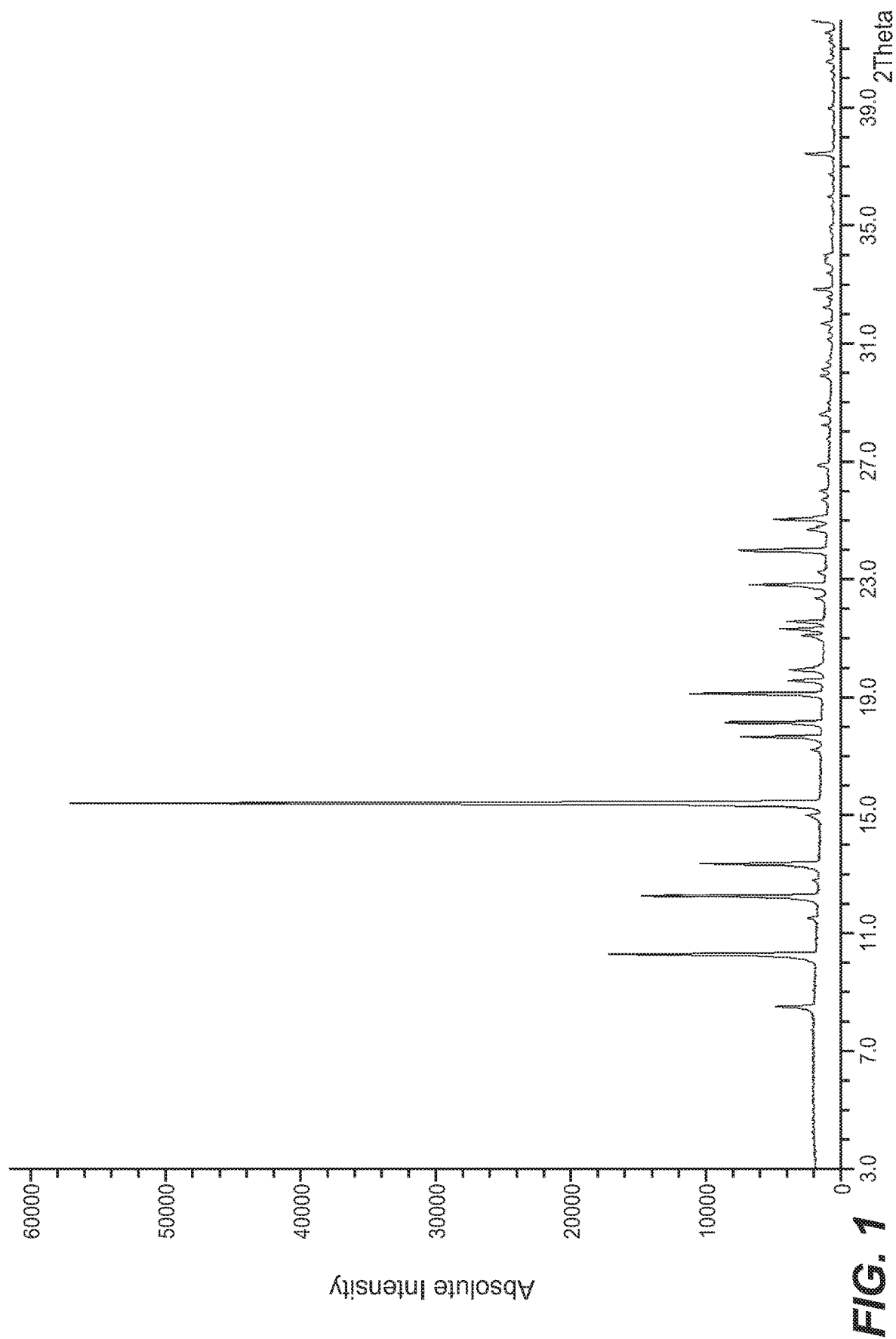
FIG. 1 illustrates a X-ray powder diffraction pattern of 2-(4-Ethyl-6-methylpyrazolo[1,5-a]pyrazin-2-yl)-9-methyl-7-(1-methylpiperidin-4-yl)-4H-pyrido[1,2-a]pyrimidin-4-one crystalline form, also known as Form A.

In a first aspect, the present invention provides a process for the preparation of a compound of formula (I):

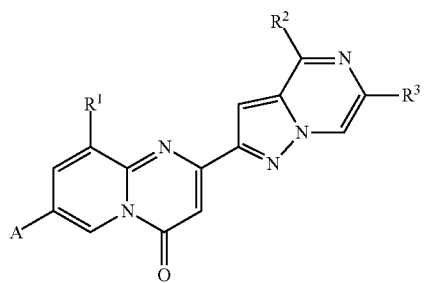

(I)

which comprises reacting compound of formula (II):

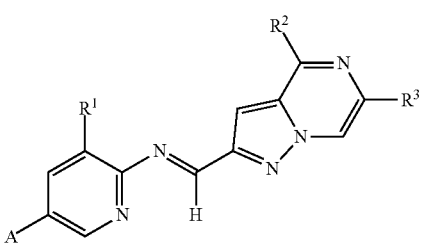

(II)

with a compound of formula (III):

(III)

wherein
$R^1$ is hydrogen, $C_{1-7}$-alkyl, or $C_{3-8}$-cycloalkyl, in particular $R^1$ is methyl;
$R^2$ is hydrogen, halo, $C_{1-7}$-alkyl, $C_{1-7}$-haloalkyl or $C_{3-8}$-cycloalkyl, in particular $R^2$ is ethyl;
$R^3$ is hydrogen or $C_{1-7}$-alkyl, in particular $R^3$ is methyl;
$R^4$ is $C_{1-7}$-alkoxy (in particular methoxy);
A is

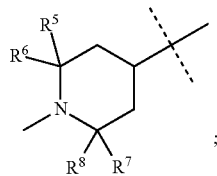

;

$R^5$ to $R^8$ are each independently selected from hydrogen and $C_{1-3}$-alkyl, in particular $R^5$ to $R^8$ are hydrogen.

In particular, the preparation of compound of formula (I) and (I') is being carried out in the presence of a tertiary amine, particularly wherein the tertiary amine is selected from diisopropylethylamine, triethylamine, 2,6-lutidine and N-methylmorpholine, more particularly diisopropylethylamine or triethylamine.

In a particular embodiment, the present invention provides a process as described herein, wherein 1 to 6 equivalents, more particularly 1.0 to 3 equivalents of a compound of formula (III) with respect to compound of formula (II) or formula (II') is used.

In another embodiment, the present invention provides a process as described above for the preparation of compound of formula (I) and (I') as described herein, wherein the compound of formula (III) with $R^4$ being $C_{1-7}$-alkoxy (in particular methoxy) or wherein the compound of formula (III$_b$), is being carried out in the presence of a tertiary amine, particularly wherein the tertiary amine is selected from diisopropylethylamine, triethylamine, 2, 6-lutidine and N-methylmorpholine, more particularly triethylamine. The present process is carried out with 3 to 20 equivalents, more particularly with 8 to 17 equivalent of a tertiary amine with respect to the compound of formula (II) or (II'). Most particularly 15 equivalent of a triethylamine with respect to the compound of formula (II) or (II') is used.

In another embodiment, the present invention provides a process as described above for the preparation of compound of formula (I) and (I'), wherein the compound of formula (III) with $R^4$ being $C_{1-17}$-alkoxy (in particular methoxy) or wherein the compound of formula (III$_b$), wherein the reaction is carried out at a temperature between 20° C. to 150° C., particularly between 50° C. to 110° C., more particularly between 80° C. and 90° C.

In a more particular embodiment, the present invention provides a process as described above for the preparation of compound of formula (I) and (I'), wherein the compound of formula (III) with $R^4$ being $C_{1-7}$-alkoxy (in particular methoxy) or wherein the compound of formula (III$_b$) is added at −10° C., then the reaction mixture is heated to 80° C.

The compounds of formula (I) are valuable pharmaceutical compounds, in particular 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one, as described in WO2013119916.

Unless otherwise stated, the following terms used in the specification and claims have the meanings given below:

The term "halo" means chloro, bromo or iodo.

"Aryl" means a monovalent monocyclic or bicyclic aromatic hydrocarbon moiety. More specifically the term aryl includes, but is not limited to, phenyl, 1-naphthyl, 2-naphthyl, and the like, more particularly phenyl.

"$C_{1-7}$alkyl" refers to a branched or straight hydrocarbon chain containing from 1 to 7 carbon atoms, such as methyl, ethyl, n-propyl, isopropyl, n-butyl, isobutyl, sec-butyl and t-butyl, pentyl, hexyl, heptyl.

"$C_{3-8}$cycloalkyl" refers to a single saturated carbocyclic ring, such as cyclopropyl, cyclobutyl, cyclopentyl, cyclohexyl, cycloheptyl and cyclooctyl.

"$C_{1-7}$haloalkyl" refers to an alkyl, as defined above, substituted with one or more halogen atoms, particularly with one to three halogen atoms. More particularly ($C_{1-7}$) haloalkyl is the chloro- and fluoro-($C_{1-7}$)alkyl.

"$C_{1-7}$alkoxy" is understood as being an —O—($C_{1-7}$)alkyl wherein ($C_{1-7}$)alkyl is as above defined, such as methoxy, ethoxy or isopropoxy.

"base" refers to a chemical compound that deprotonates another compound when reacted with it. Suitable bases for use in accordance with this disclosure include but are not limited to, e.g., tertiary amines and basic alkali metal salts. In some embodiments, the tertiary amines include triethylamine, N-methylmorpholine and diisopropylethylamine. In some embodiments, the basic alkali metal salts include, e.g., sodium carbonate (Na2CO3), potassium carbonate (K2CO3), sodium bicarbonate (NaHCO$_3$), sodium and potassium alkoxides including, but not limited to, sodium and potassium t-butoxide, npropoxide, i-propoxide, ethoxide, methoxide, and the like, sodium amide (NaNH2), potassium amide (KNH2), and the like.

"reducing agent" refers to a hindered organoborane, an organo-aluminium hydride or inorgano-aluminium hydride.

"hindered organoborane" refers particularly to alkali metal tri-($C_{1-7}$)alkyl or tri-aryl borohydride reducing agents, such as, for example, lithium tri-sec-butylborohydride, lithium trisiamylborohydride or lithium triphenylborohydride, or the corresponding reducing agents with lithium replaced by potassium or sodium. Examples of hindered organoboranes are lithium tri-sec-butylborohydride (L-Selectride), potassium tri-sec-butylborohydride (K-Selectride), sodium tri-sec-butylborohydride (N-Selectride), lithium trisiamylborohydride (LS-Selectride), potassium trisiamylborohydride (KS-Selectride), potassium triphenylborohydride and lithium triphenylborohydride.

"organo-aluminium hydride" refers to a reducing agent containing aluminium and hydride moieties and organic groups (e.g. ($C_{1-7}$)alkyl or "($C_{1-7}$)alkoxy, suitably containing from 1 to 7 carbon atoms), such as sodium bis-(2-methoxyethoxy)aluminium hydride (Red-Al®), diisobutyl-aluminium hydride (DIBAL) or lithium tri-tert-butoxyaluminohydride (LTBA). Particularly the organo-aluminium hydrides for use in the present invention are Red-Al®, DIBAL and LTBA.

"inorgano-aluminium hydride" refers to a reducing agent containing aluminium and hydride moieties and inorganic groups such as Sodium or Lithium, such as sodium aluminum hydride or Lithium aluminum hydride (LiAlH$_4$). Particularly the inorgano-aluminium hydride for use in the present invention is LiAlH$_4$.

"Transition metal hydrogenation catalyst" refers to a transition metal hydrogenation catalyst, which acts in a different phase than the substrate. Especially the transition metal hydrogenation catalyst is in the solid phase. In particular while the transition metal hydrogenation catalyst is in the solid phase, the reactants are in the liquid phase. The transition metal hydrogenation catalyst contains a transition metal which forms one or more stable ions, which have incompletely filled d orbitals (i.e. Pd, Pt, Rh, Au, Ni, Co, Ru, Ir) in particular noble metal, such as Pd, Pt, Rh or Au. In these catalysts the transition metal is in particular "supported", which means that the catalyst is dispersed on a second material that enhances the effectiveness. The "support" can be merely a surface on which the metal is spread to increase the surface area. The supports are porous materials with a high surface area, most commonly alumina or various kinds of carbon. Further examples of supports include, but are not limited to, silicon dioxide, titanium dioxide, calcium carbonate, barium sulfate, diatomaceous earth and clay. The metal itself can also act as a support, if no other support is present. More specifically the term "Transition metal hydrogenation catalyst" includes but is not limited to, a Raney catalyst (e.g. Ra—Ni, Ra—Co) Pd/C, Pd(OH)$_2$/C, Au/TiO$_2$, Rh/C, Ru/Al$_2$O$_3$, Ir/CaCO$_3$, or Pt/C, in particular Pd/C.

"solvate" and "pseudo-polymorph" can be used synonymously to refer a crystal having either stoichiometric or nonstoichiometric amounts of a solvent incorporated in the crystal lattice. If the incorporated solvent is water, the solvate formed is a "hydrate". When the incorporated solvent is alcohol, the solvate formed is an "alcoholate".

"XRPD" refers the analytical method of X-Ray Powder Diffraction. The repeatability of the angular values is in the range of 2Theta+0.2°. The term "approximately" given in combination with an angular value denotes the repeatability which is in the range of 2Theta+0.2°. The relative XRPD peak intensity is dependent upon many factors such as structure factor, temperature factor, crystallinity, polarization factor, multiplicity, and Lorentz factor. Relative intensities may vary considerably from one measurement to another due to preferred orientation effects. According to USP 941 (US Pharmacopoeia, 37th Edition, General Chapter 941), relative intensities between two samples of the same material may vary considerably due to "preferred orientation" effects. Anisotropic materials adopting preferred orientation will lead to anisotropic distribution of properties such as modulus, strength, ductility, toughness, electrical conductivity, thermal expansion, etc., as described e.g. in Kocks U. F. et al. (Texture and Anisotropy: Preferred Orientations in Polycrystals and Their Effect on Materials Properties, Cambridge University Press, 2000). In XRPD but also Raman spectroscopy, preferred orientations cause a change in the intensity distribution. Preferred orientation effects are particularly pronounced with crystalline APIs of relatively large particle size.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

The term "buffer" denotes a pharmaceutically acceptable excipient, which stabilizes the pH of a pharmaceutical preparation. Suitable buffers are well known in the art and can be found in the literature. Particular pharmaceutically acceptable buffers comprise histidine-buffers, arginine-buffers, citrate-buffers, succinate-buffers, acetate-buffers and phosphate-buffers. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The term "antioxidant" denotes pharmaceutically acceptable excipients, which prevent oxidation of the active pharmaceutical ingredient. Antioxidants comprise ascorbic acid, glutathione, cysteine, methionine, citric acid, EDTA.

The term "surfactant" denotes a pharmaceutically acceptable excipient which is used to protect protein compositions against mechanical stresses like agitation and shearing. Examples of pharmaceutically acceptable surfactants include poloxamers, polysorbates, polyoxyethylene alkyl ethers (BRIJ®), alkylphenylpolyoxyethylene ethers (TRITON-X®) or sodium dodecyl sulfate (SDS).

"ambient conditions" refers conditions as experienced in a standard laboratory, e.g. atmospheric pressure, air, ambient temperature between 18° C. and 28° C., humidity between 30% rH and 80% rH.

"Form A" as used herein refers the crystalline anhydrous polymorphic Form A of 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one.

"Form F" as used herein refers the crystalline anhydrous polymorphic Form F of 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one.

In particular, the invention relates to a process as described herein, wherein the compound of formula (I) is 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one.

In another embodiment, the present invention is also directed to a process for the preparation of a compound of formula (II):

(II)
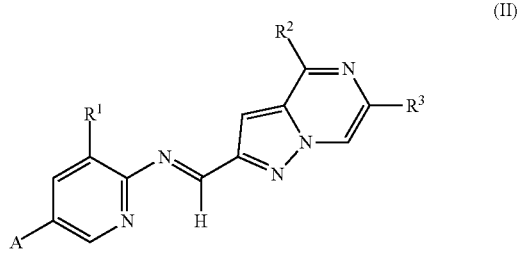

which comprises reacting compound of formula (IV)

(IV)
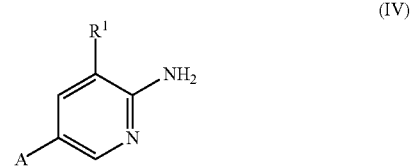

with a compound of formula (V)

(V)
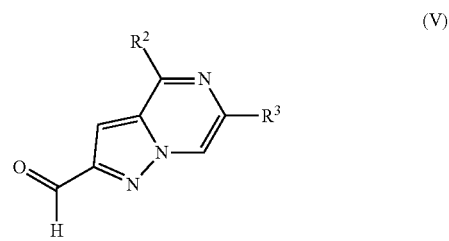

wherein, $R^1$ is hydrogen, $C_{1-7}$-alkyl, or $C_{3-8}$-cycloalkyl, in particular $R^1$ is methyl;

$R^2$ is hydrogen, halo, $C_{1-7}$-alkyl, $C_{1-7}$-haloalkyl or $C_{3-8}$-cycloalkyl, in particular $R^2$ is ethyl;

$R^3$ is hydrogen or $C_{1-7}$-alkyl, in particular $R^3$ is methyl;

A is

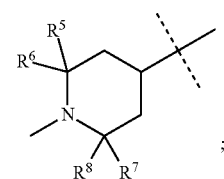;

$R^5$ to $R^8$ are each independently selected from hydrogen and $C_{1-3}$-alkyl, in particular $R^5$ to $R^8$ are hydrogen.

In yet another embodiment, the present invention is also directed to a process for the preparation of a compound of formula (V):

(V)
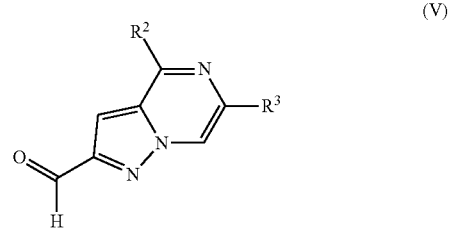

which comprises reacting a compound of formula (VIII):

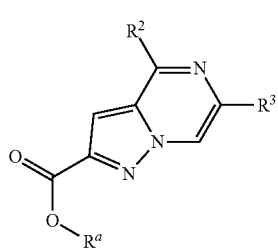
(VII)

wherein $R^2$ and $R^3$ are as defined previously and $R^a$ is $C_{1-7}$-alkyl, particularly methyl or ethyl, with a reducing agent. In particular, the process is followed by a crystallisation step in water.

In a particular embodiment, the present invention provides a process for the preparation of a compound of formula (I):

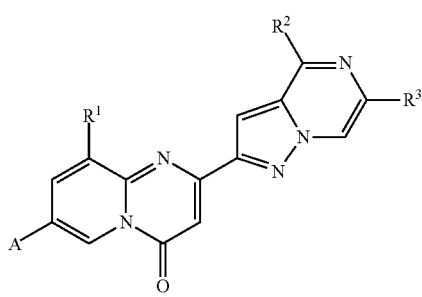
(I)

comprising:

a) reacting a compound of formula (IV)

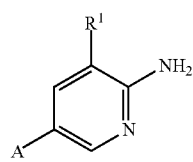
(IV)

with a compound of formula (V)

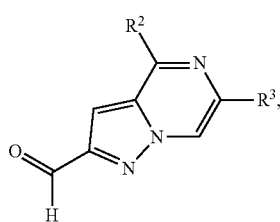
(V)

to obtain a compound of formula (II):

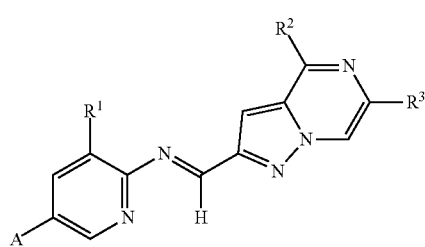
(II)

b) reacting a compound of formula (II)

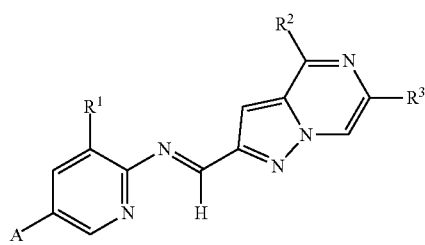
(II)

with a compound of formula (III):

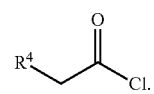
(III)

wherein, $R^1$ is hydrogen, $C_{1-7}$-alkyl, or $C_{3-8}$-cycloalkyl, in particular $R^1$ is methyl;

$R^2$ is hydrogen, halo, $C_{1-7}$-alkyl, $C_{1-7}$-haloalkyl or $C_{3-8}$-cycloalkyl, in particular $R^2$ is ethyl;

$R^3$ is hydrogen or $C_{1-7}$-alkyl, in particular $R^3$ is methyl;

$R^4$ is $C_{1-7}$-alkoxy (in particular methoxy);

A is

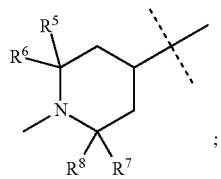

$R^5$ to $R^8$ are each independently selected from hydrogen and $C_{1-3}$-alkyl, in particular $R^5$ to $R^8$ are hydrogen.

In a particular embodiment, the present invention provides the process herein described wherein steps a) and b) are telescoped.

Compound of formula (IV) wherein $R^1$, $R^5$, $R^6$, $R^7$, $R^8$ and A are as defined previously, X is I, Br, Cl or F, particularly Br, can be prepared in accordance to scheme 1.

Scheme 1:

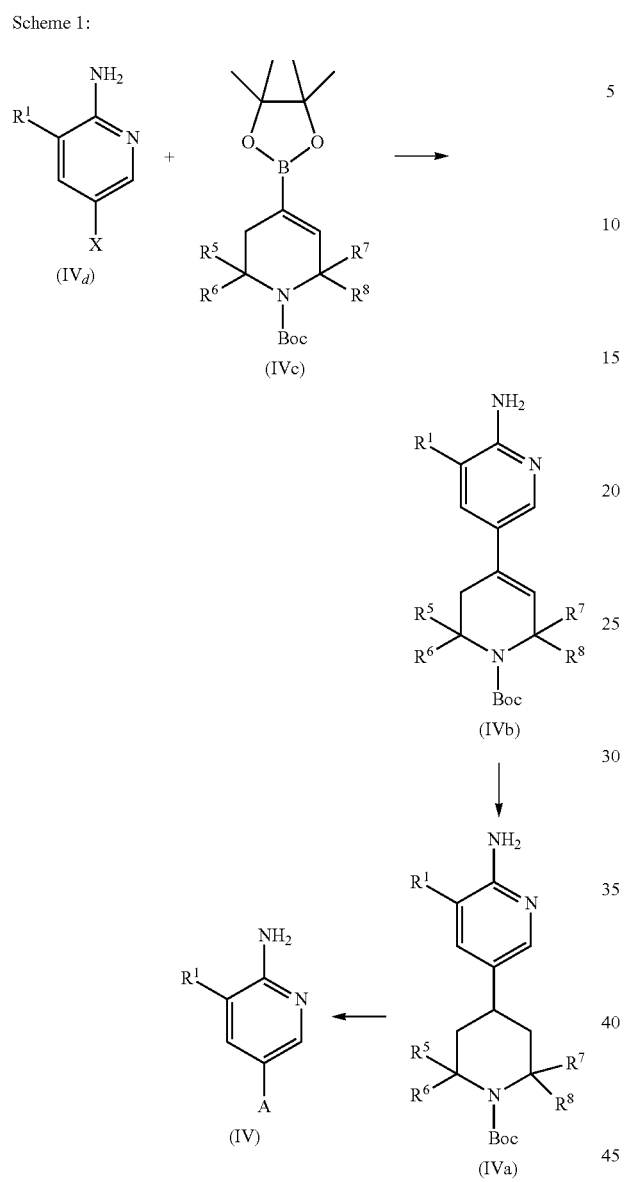

Scheme 2.

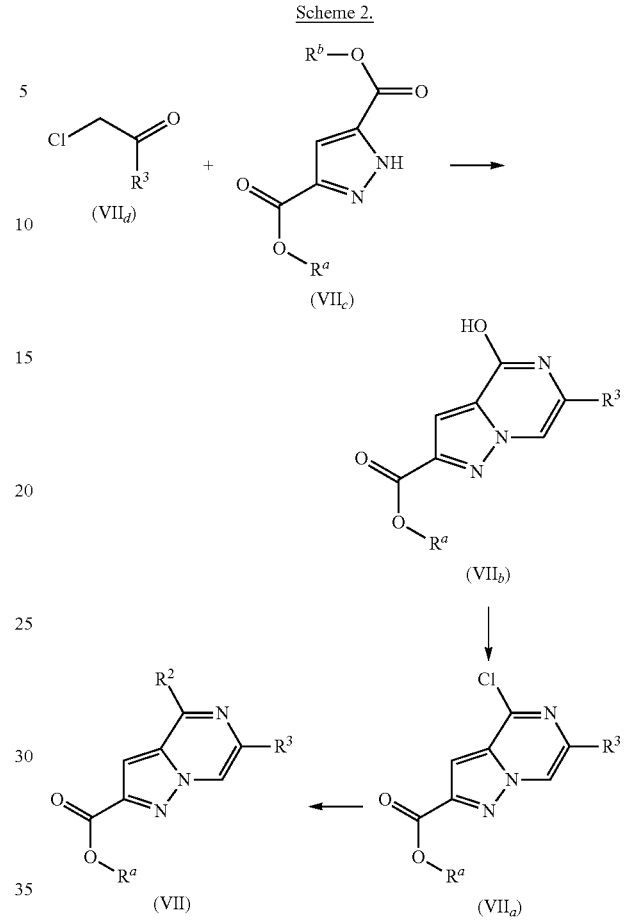

In particular, a compound (VIIc) is reacted with a compound (VIId) in the presence of a base (such as $Cs_2CO_3$) in a suitable solvent (such as acetone and the like), followed by the addition of ammonium acetate in suitable solvent (such as DMSO) to provide a compound (VIIb). Compound (VIIb) is then further treated with a chlorinated reagent (such as $POCl_3$) to provide a compound (VIIa). A compound of formula (VIIa) is reacted with a boronic acid derivative of formula $R^2B(OH)_2$ or boronic acid ester derivative of formula $R^2$bis(pinacolato)diboron, in the presence of a catalyst (such as Pd(dppf)$Cl_2$ and the like) and a base (such as $K_2CO_3$ and the like) in a suitable solvent (such as anisole, toluene and the like), undergoing a Suzuki cross coupling to give Compound (VII).

In another embodiment, the present invention provides a compound of formula (II):

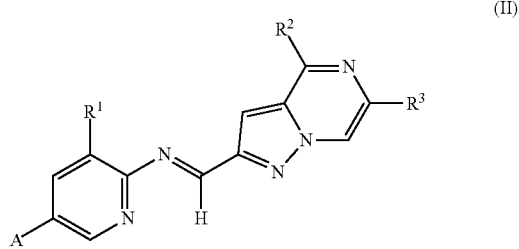

In particular, compound IVb can be prepared by reacting a compound (IVd) with a compound (IVc), in the presence of a catalyst (such as Pd(PPh$_3$)$_4$, Pd(OAc)$_2$, Pd$_2$(dba)$_3$, Pd(PPh$_3$)$_2$Cl$_2$, PdCl$_2$(dppf), PdCl$_2$(dppf).CH$_2$Cl$_2$, PdCl$_2$(dppp), in particular in the presence of PdCl$_2$(dppf) or its CH$_2$Cl$_2$ adduct; and a base (such as Na2CO3, K2CO3, Cs2CO3, KOtBu, KOAc; in particular K$_2$CO$_3$). Compound (IVa) can be prepared by reduction of compound (IVb) in the presence of a heterogeneous transition metal hydrogenation catalyst (such as Pd/C) and hydrogen gas. Compound (IV) can be prepared by reduction of the Boc (tert-Butoxycarbonyl) group of compound (IVa) with the use of a reducing agent (such as LiAlH$_4$, DIBAH or Red-Al®, in particular with LiAlH$_4$) Compound of formula (VII) wherein $R^2$, $R^3$ and $R^a$ are as defined previously, Rb is $C_{1-7}$-alkyl, can be prepared according to procedures described in WO2013119916, in particular in accordance to scheme 2.

wherein
R¹ is hydrogen, $C_{1-7}$-alkyl, or $C_{3-8}$-cycloalkyl, in particular R¹ is methyl;
R² is hydrogen, halo, $C_{1-7}$-alkyl, $C_{1-7}$-haloalkyl or $C_{3-8}$-cycloalkyl, in particular R² is ethyl;
R³ is hydrogen or $C_{1-7}$-alkyl, in particular R³ is methyl;
A is

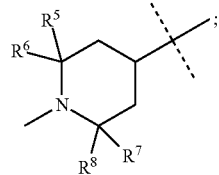

R⁵ to R⁸ are each independently selected from hydrogen and $C_{1-3}$-alkyl, in particular R⁵ to R⁸ are hydrogen.

In another embodiment, the present invention provides a compound of formula (IV):

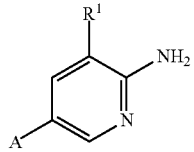
(IV)

wherein
R¹ is hydrogen, $C_{1-7}$-alkyl, or $C_{3-8}$-cycloalkyl, in particular R¹ is methyl;
A is

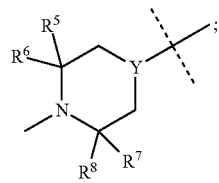

R⁵ to R⁸ are each independently selected from hydrogen and $C_{1-3}$-alkyl, in particular R⁵ to R⁸ are hydrogen.

In another embodiment, the present invention provides a compound of formula (V)

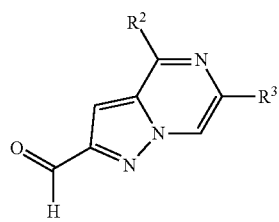
(V)

wherein
R² is hydrogen, halo, $C_{1-7}$-alkyl, $C_{1-7}$-haloalkyl or $C_{3-8}$-cycloalkyl, in particular R² is ethyl;
R³ is hydrogen or $C_{1-7}$-alkyl, in particular R³ is methyl.

In another embodiment, the present invention provides a process for the preparation of a compound of formula (I'):

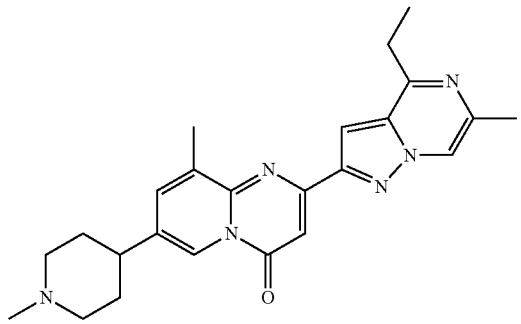
(I')

which comprises reacting compound of formula (II'):

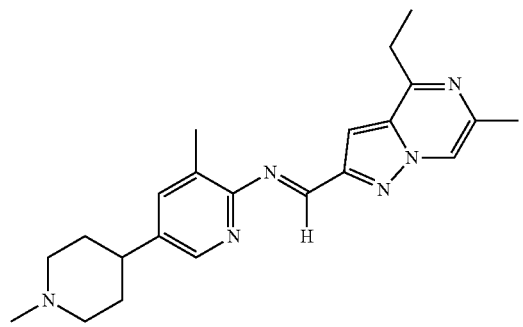
(II')

with a compound of formula (III$_b$):

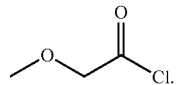
(III$_b$)

In another embodiment, the present invention is also directed to a process for the preparation of a compound formula (II'):

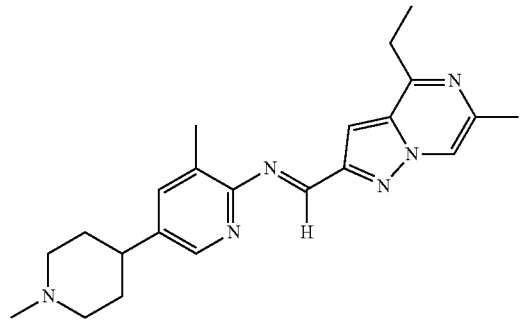
(II')

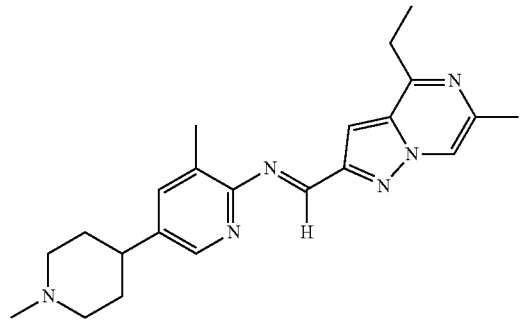

which comprises reacting compound of formula (IV')

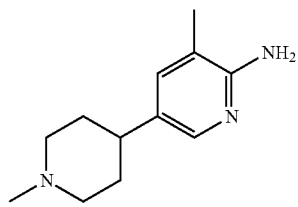
(IV')

with a compound of formula (V')

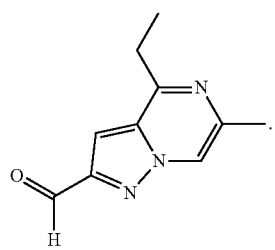
(V')

In a particular embodiment, the present invention provides a process for the preparation of a compound of formula (I'):

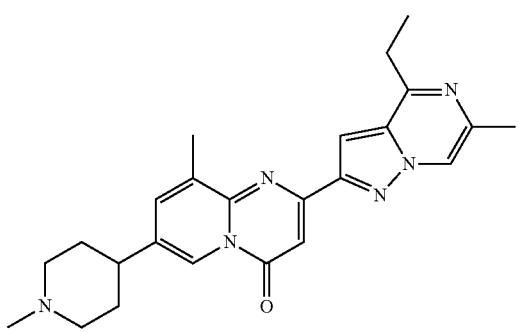
(I')

comprising:
a) reacting compound of formula (IV')

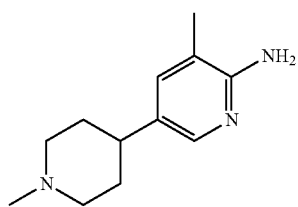
(IV')

with a compound of formula (V')

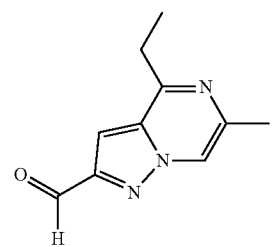
(V')

to obtain a compound of formula (II'):

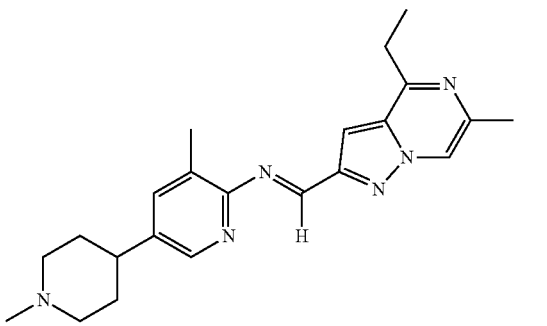
(II')

b) reacting the compound of formula (II') with a compound of formula (III$_b$):

(III$_b$)

In a particular embodiment, the present invention provides the process herein described wherein steps a) and b) are telescoped.

The present application discloses a process for the preparation of a compound of formula (I'):

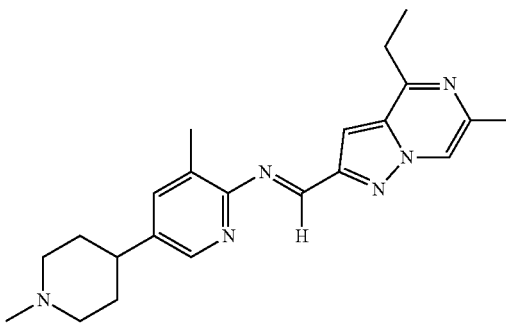
(I')

which comprises reacting compound of formula (II'):

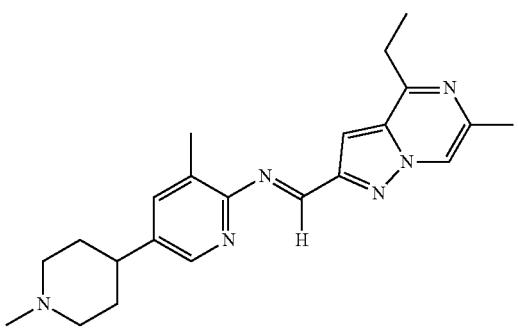
(II')

with a compound of formula (III$_a$):

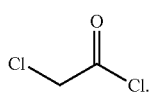

According to the process herein described when compound (III$_a$) is being used compounds of formulae (X) and (XI) may be produced as side-products, which are genotoxic:

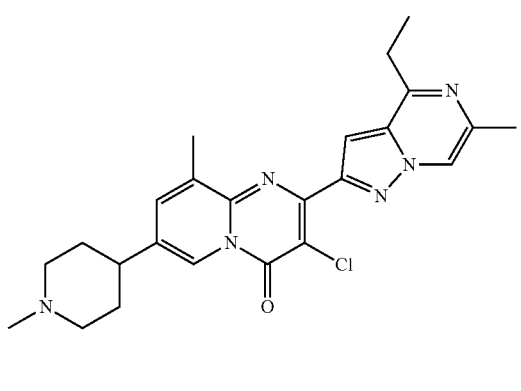

In yet another embodiment, the present invention is also directed to a process for the preparation of a compound of formula (V'):

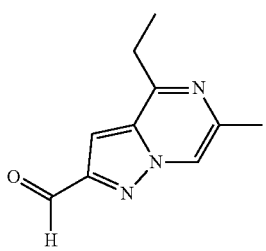

which comprises reacting a compound of formula (VII')

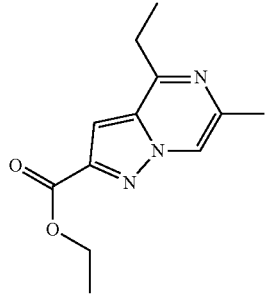

with a reducing agent.

In a particular embodiment, the application discloses the process of making a compound of formula (IV') wherein X, is I, Br, Cl or F, particularly Br, in accordance to scheme 3.

Scheme 3:

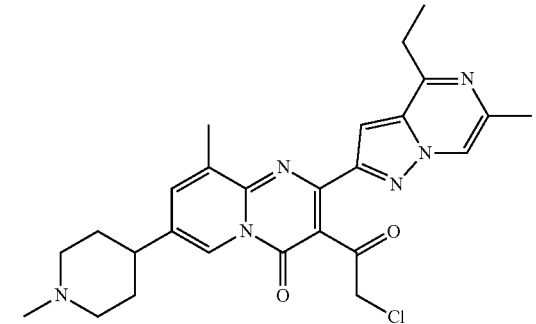

In particular, compound (IV'$_b$) can be prepared by reacting a compound (IV'$_d$) with a compound (IV'$_c$), in the presence of a catalyst (such as Pd(PPh$_3$)$_4$, Pd(OAc)$_2$, Pd$_2$(dba)$_3$, Pd(PPh$_3$)$_2$Cl$_2$, PdCl$_2$(dppf), PdCl$_2$(dppf).CH$_2$Cl$_2$, PdCl$_2$(dppp), in particular in the presence of PdCl$_2$(dppf) or its CH$_2$Cl$_2$ adduct) and a base (such as Na$_2$CO$_3$, K$_2$CO$_3$, Cs$_2$CO$_3$, KOtBu, KOAc; in particular K$_2$CO$_3$). Compound (IV'$_a$) can be prepared by reduction of compound (IV'b) in the presence of a transition metal hydrogenation catalyst (such as Pd/C) and hydrogen gas. Compound (IV') can be prepared by reduction of the Boc (tert-Butoxycarbonyl)

group of compound (IV'<sub>a</sub>) with the use of a reducing agent (such as LiAlH$_4$, DIBAH or Red-Al in particular with LiAlH$_4$).

In a particular embodiment, the application discloses the process of making a compound of formula (VII'), in accordance to scheme 4.

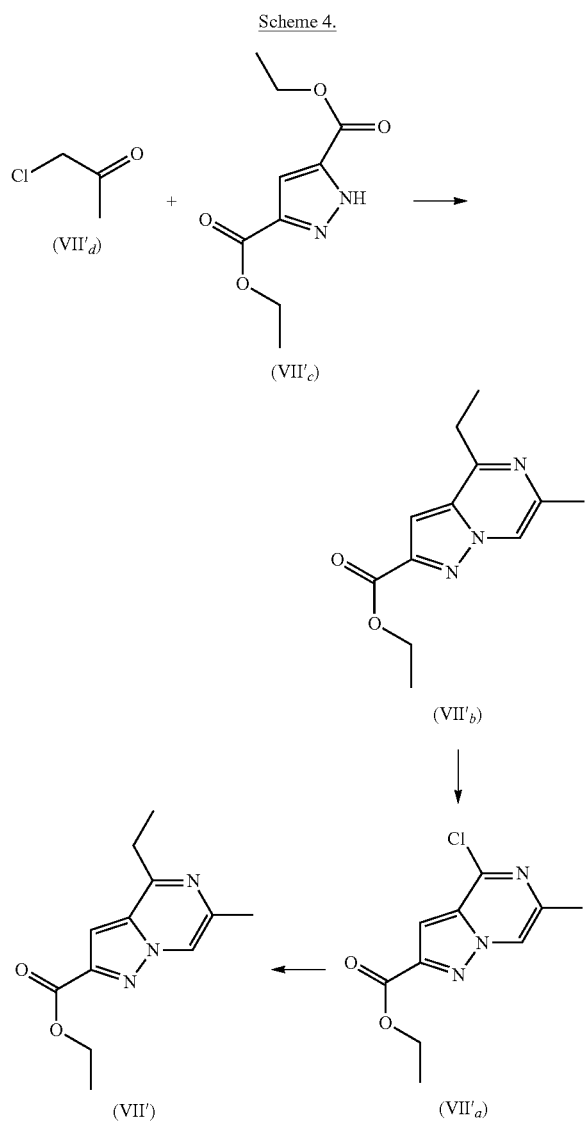

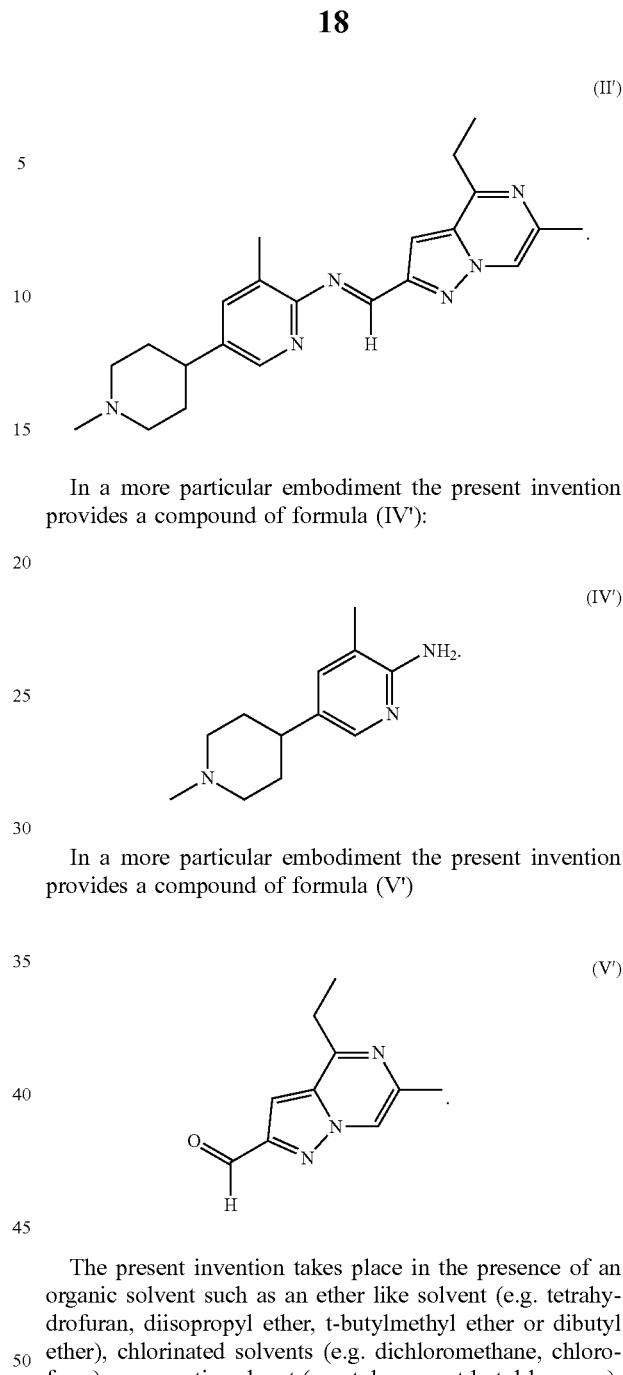

In particular, a compound (VII'c) is reacted with a compound (VII'd) in the presence of a base (such as Cs$_2$CO$_3$) and a suitable solvent (such as acetone and the like), followed by the addition of ammonium acetate in suitable solvent (such as DMSO) to provide a compound (VII'b). Compound (VII'b) is then further treated with a chlorinated reagent (such as POCl$_3$) to provide a compound (VII'a). A compound of formula (VII'a) is reacted with a boronic acid derivative of formula EtB(OH)$_2$, in the presence of a catalyst (such as Pd(dppf)Cl$_2$ and the like) and a base (such as K$_2$CO$_3$ and the like) in a suitable solvent (such as anisole, toluene and the like), undergoing Suzuki cross coupling to give Compound (VII).

In a more particular embodiment, the present invention provides a compound of formula (II'):

In a more particular embodiment the present invention provides a compound of formula (IV'):

In a more particular embodiment the present invention provides a compound of formula (V')

The present invention takes place in the presence of an organic solvent such as an ether like solvent (e.g. tetrahydrofuran, diisopropyl ether, t-butylmethyl ether or dibutyl ether), chlorinated solvents (e.g. dichloromethane, chloroform) or aromatic solvent (e.g. toluene or t-butyl-benzene). In particular, the solvent to be used for the preparation of a compound of formula (I) is toluene.

The reactions are performed in particular under an inert gas atmosphere, more particularly under argon or nitrogen.

In a further embodiment the present invention provides a process for the preparation of 2-(4-Ethyl-6-methyl-pyrazolo [1,5-a]pyrazin-2-yl)-9-methyl-7-(1-methyl-piperidin-4-yl)-pyrido[1,2-a]pyrimidin-4-one comprising the formation of a compound of formula (I) obtained by any of the processes and conditions mentioned previously.

Furthermore the present invention comprises the crystallization step as described herein. 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one was found to crystallize in different crystal structures as pure compound (polymorphs). It was also found that 2-(4-Ethyl-6-methyl-pyrazolo[1,5-a]

pyrazin-2-yl)-9-methyl-7-(1-methyl-piperidin-4-yl)-pyrido[1,2-a]pyrimidin-4-one can form solvates or hydrates (pseudo-polymorphs). In particular the following solvents were found to form solvates: ethanol, 1-propanol, 1-butanol, dichloromethane, chloroform, 1,4-dioxane, toluene, benzene, acetic acid.

In another aspect, the present invention provides 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one in polymorphs Form A and Form F. It was found that Form A and Form F are enantiotropically related with Form F being more stable at 80° C. or below. Form F was surprisingly found to improve drug product robustness.

In another embodiment, the present invention provides 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one in crystalline Form A or Form F.

In a particular embodiment, the present invention provides -(4-Ethyl-6-methyl-pyrazolo[1,5-a]pyrazin-2-yl)-9-methyl-7-(1-methyl-piperidin-4-yl)-pyrido[1,2-a]pyrimidin-4-one in polymorphic Form A characterized by an X-ray powder diffraction pattern (XRPD) having peaks at an angle of diffraction 2-theta at about 10.3°, 12.30°, 13.3°, and 15.4° (+0.2°).

In particular embodiment, Form A is characterized by XRPD diffraction pattern of comprising XRPD peaks at angles of diffraction 2Theta of as denoted in Table 2. In a particular embodiment, Form A is characterized by the XRPD diffraction pattern of FIG. 1

Table 1 lists the relevant crystal structure data of Form A. The lattice constants, unit cell volume and calculated density are based on low temperature data.

TABLE 1

Single Crystal Structural Data of Form A

| | | |
|---|---|---|
| Crystal form | | Form A |
| Solid form description | | plate |
| Measuring Temperature | | 89(2) K |
| Crystal system | | Monoclinic |
| Space group | | P2(1) c |
| Unit cell dimensions: | a | 10.244(2) Å |
| | b | 9.3320(19) Å |
| | c | 22.582(5) Å |
| | α | 90° |
| | β | 91.64(3)° |
| | γ | 90° |
| Cell volume | | 2157.9(7) Å³ |
| API molecules in unit cell | | 4 |
| Calculated density | | 1.282 g/cm³ |

TABLE 2

XRPD of Form A:
Form A

| 2Theta/° | rel. int./% * |
|---|---|
| 8.5 | 9 |
| 10.3 | 30 |
| 12.3 | 27 |
| 13.3 | 18 |
| 15.4 | 100 |
| 17.7 | 13 |
| 18.1 | 15 |
| 19.1 | 20 |
| 19.6 | 7 |
| 19.9 | 7 |
| 21.1 | 5 |
| 21.3 | 8 |

TABLE 2-continued

XRPD of Form A:
Form A

| 2Theta/° | rel. int./% * |
|---|---|
| 21.5 | 7 |
| 22.8 | 12 |
| 24.0 | 14 |
| 25.0 | 9 |

* Relative intensities may vary considerably from one measurement to another

In a particular embodiment, the present invention provides -(4-Ethyl-6-methyl-pyrazolo[1,5-a]pyrazin-2-yl)-9-methyl-7-(1-methyl-piperidin-4-yl)-pyrido[1,2-a]pyrimidin-4-one in polymorphic Form F characterized by an XRPD having peaks at an angle of diffraction 2-theta at about 8.0°, 9.1°, 15.00, and 23.7°(±0.20).

Figure 2:
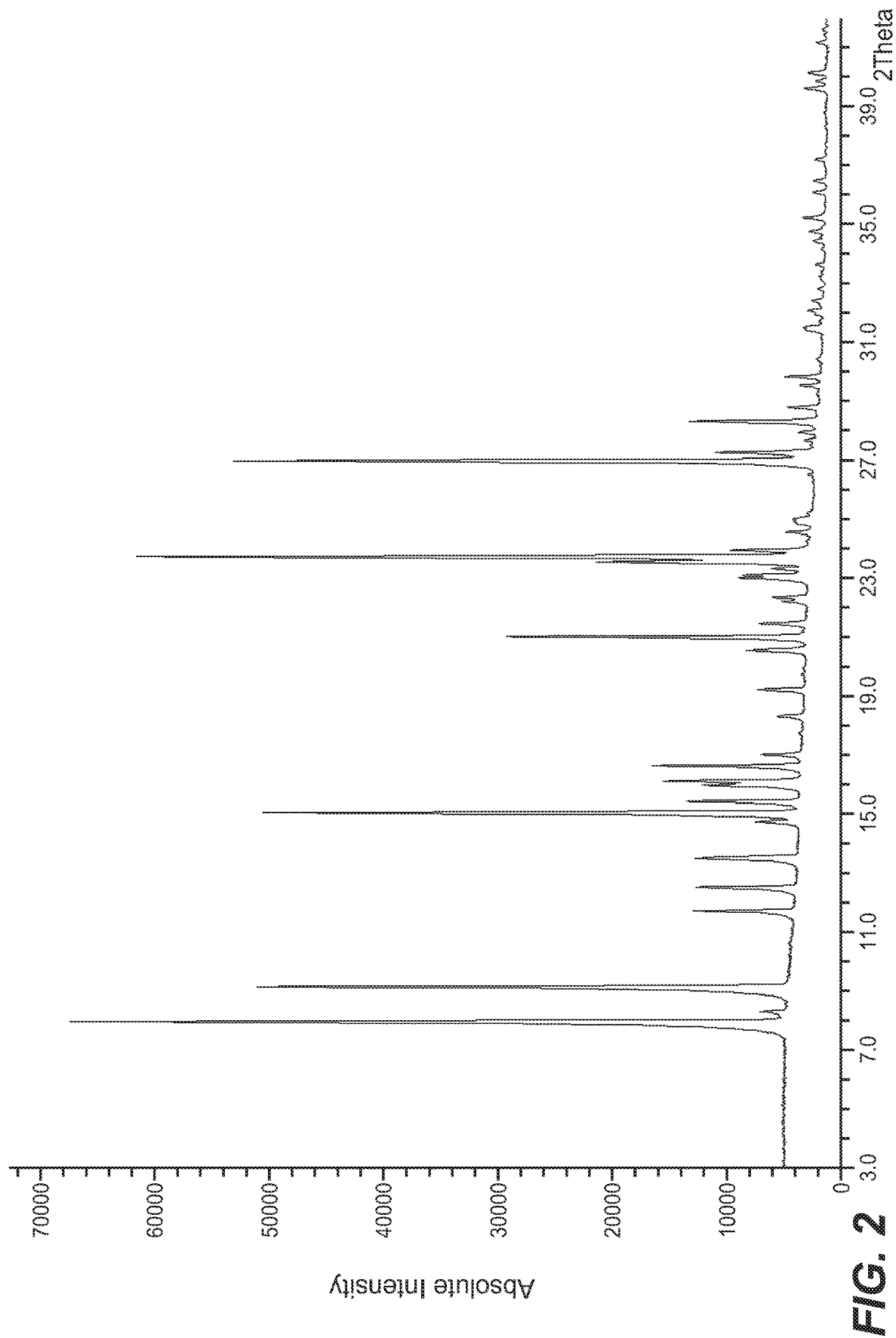
FIG. 2 illustrates a X-ray powder diffraction pattern of 2-(4-Ethyl-6-methylpyrazolo[1,5-a]pyrazin-2-yl)-9-methyl-7-(1-methylpiperidin-4-yl)-4H-pyrido[1,2-a]pyrimidin-4-one crystalline form, also known as Form F.

In particular embodiment, Form F is characterized by XRPD diffraction pattern of comprising XRPD peaks at angles of diffraction 2Theta of as denoted in Table 4. In a particular embodiment, Form F is characterized by the XRPD diffraction pattern of FIG. 2.

Table 3 lists the relevant crystal structure data of Form F. The lattice constants, unit cell volume and calculated density are based on ambient temperature data.

TABLE 3

Single Crystal Structural Data of Form F

| | | |
|---|---|---|
| Crystal form | | Form F |
| Solid form description | | needle |
| Measuring Temperature | | 293(2) K |
| Crystal system | | Triclinic |
| Space group | | P1 |
| Unit cell dimensions: | a | 8.5790(9) Å |
| | b | 11.522(2) Å |
| | c | 12.3296(18) Å |
| | α | 67.707(15)° |
| | β | 75.417(11)° |
| | γ | 84.278(11)° |
| Cell volume | | 1091.3(3) Å³ |
| API molecules in unit cell | | 2 |
| Calculated density | | 1.268 g/cm³ |

TABLE 4

XRPD of Form F:
Form F

| 2Theta/° | rel. int./% * |
|---|---|
| 8.0 | 100 |
| 8.3 | 10 |
| 9.1 | 75 |
| 11.7 | 19 |
| 12.5 | 19 |
| 13.5 | 19 |
| 14.7 | 11 |
| 15.0 | 75 |
| 15.4 | 20 |
| 16.0 | 18 |
| 16.1 | 23 |
| 16.6 | 24 |
| 17.0 | 10 |
| 19.2 | 11 |
| 20.6 | 12 |
| 21.0 | 43 |
| 21.5 | 11 |
| 23.0 | 13 |
| 23.1 | 13 |
| 23.6 | 32 |
| 23.7 | 89 |

TABLE 4-continued

XRPD of Form F:
Form F

| 2Theta/° | rel. int./% * |
|---|---|
| 23.9 | 15 |
| 27.0 | 76 |
| 27.3 | 15 |
| 28.3 | 20 |

* Relative intensities may vary considerably from one measurement to another

Analytical Methods

X-Ray Powder Diffraction

X-ray diffraction patterns are recorded at ambient conditions in transmission geometry with a STOE STADI P diffractometer (Cu Ku radiation, primary monochromator, silicon strip detector, angular range 3° to 42° 2-theta, approximately 30 minutes total measurement time). The samples (approximately 10 to 50 mg) are prepared between thin polymer films and are analyzed without further processing (e.g. grinding or sieving) of the substance.

Single Crystal Structure Analysis

For single crystal structure analysis a single crystal sample was mounted in a kapton loop on a goniometer and measured at ambient conditions. Alternatively, the crystal was cooled in a nitrogen stream during measurement. Data were collected on a GEMINI R Ultra diffractometer from Rigaku Oxford Diffraction. Cu-radiation of 1.54 Å wavelength was used for data collection. Data was processed with the Rigaku Oxford Diffraction CRYSALIS software. The crystal structure was solved and refined with standard crystallographic software. In this case the program ShelXTL from Bruker AXS (Karlsruhe) was used.

The present invention provides the process for the preparation of polymorph Form A, Form F, solvent-related solvates (pseudo-polymorphs), or hydrates of 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one, wherein 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one is dissolved upon heating in a solvent or solvent mixture. The solution is then cooled down. A suspension is formed upon spontaneous crystallization comprising a saturated solution and a crystalline solid. The suspension is filtered, optionally washed with the respective solvent or solvent mixture and optionally dried under vacuum at elevated temperature (particularly but not exclusively at 50-60° C.).

The solvent according to the crystallisation step comprises alcohols, or mixtures of alcohols with other solvents as such as esters or water; further it comprises cyclic or linear ethers, aromatic solvents, chlorinated solvents and polar protic solvents. Different polymorphic forms, pseudo-polymorphic forms (solvates), and hydrates are known. In particular the following solvents were found to form solvates: ethanol, 1-propanol, 1-butanol, dichloromethane, chloroform, 1,4-dioxane, toluene, benzene, acetic acid.

It was found that a solvate (pseudo-polymorph) formed by spontaneous crystallization (as described above) may transform into Form F. Particularly it was found that the 1-butanol solvate transforms to Form F upon digestion in 1-Butanol/water 98/2 m/m at approx. 5° C. within approx. 2 weeks.

In another embodiment, the present invention provides a crystallization process controlled by addition of seeding crystals with known solid form (polymorph, pseudo-polymorph).

For instance 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one can be dissolved upon heating in a solvent or solvent mixture of choice, e.g., alcohols or mixtures of alcohols with other solvents as e.g., esters or water. By cooling the solution a supersaturated solution is formed. Seeding crystals of known solid form (polymorph, pseudo-polymorph) are added as dry powder or as suspension in a suitable solvent.

In a particular embodiment, the present invention provides a process for making polymorph Form A of 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one by seeding cooling crystallization from 1-butanol/water mixtures, most particularly from a 1-butanol/water 98/2 m/m mixture. In particular embodiment, the present invention provides a process of making Form A comprising:
  a) 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one is dissolved in a 1-butanol/water 98/2 m/m mixture upon heating at a temperature above 80° C., more particularly at. 85° C.
  b) cooling the solution below 80° C., more particularly to 75° C., particularly to obtain a supersaturated solution;
  c) seeding crystals of Form A are added either as dry powder or as suspension in 1-butanol or as suspension in 1-butanol/water 98/2 m/m mixture;
  d) the suspension is further cooled; and
  e) optionally the solids are filtered and vacuum-dried at elevated temperature, more particularly at 50-60° C.

In another embodiment, the present invention provides a process for making polymorph Form F of 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one by seeding cooling crystallization from 1-butanol/water mixtures, most particularly from 1-butanol/water 98/2 m/m.

In particular embodiment, the present invention provides a process of making Form F comprising:
  a) 2-(4-Ethyl-6-methyl-pyrazolo[1,5-a]pyrazin-2-yl)-9-methyl-7-(1-methyl-piperidin-4-yl)-pyrido[1,2-a]pyrimidin-4-one is dissolved in a 1-butanol/water 98/2 m/m mixture upon heating whereas at a temperature above 80° C., more particularly at 85° C.;
  b) cooling the solution below 80° C., more particularly to 75° C., particularly to obtain a supersaturated solution;
  c) seeding crystals of Form F are added either as dry powder or as suspension in 1-butanol/water 98/2 m/m mixture;
  d) the suspension is further cooled; and
  e) Optionally the solids are filtered and vacuum-dried at elevated temperature, more particularly at 50-60° C.

A particular embodiment of the invention also relates to a pharmaceutical composition comprising a solid form of the compound of formula (I') as described herein and at least one pharmaceutically acceptable excipient.

A particular embodiment of the invention also relates to a solid form of the compound of formula (I') as described herein for use as therapeutically active substances.

The starting materials and reagents, which do not have their synthetic route explicitly disclosed herein, are generally available from commercial sources or are readily prepared using methods well known to the person skilled in the art.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

Example 1: tert-butyl 4-(6-amino-5-methyl-3-pyridyl)-3,6-dihydro-2H-pyridine-1-carboxylate

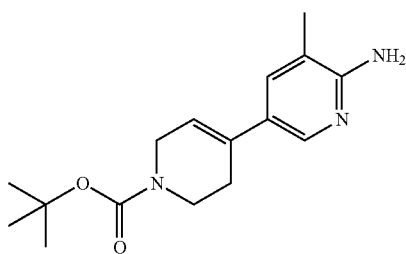 [SMILES: Cc1cc(C2=CCN(C(=O)OC(C)(C)C)CC2)cnc1N]

5-bromo-3-methylpyridin-2-amine (14.8 kg, 79.1 mol), tert-butyl 4-(4,4,5,5-tetramethyl-1,3,2-dioxaborolan-2-yl)-5,6-dihydropyridine-1(2H)-carboxylate (24.5 kg, 79.1 mol) and potassium carbonate (33.0 kg, 238.5 mol) were suspended in water (110 l) and acetonitrile (360 l) and the suspension was heated to 70° C. [1,1'-Bis(diphenylphosphino)ferrocene]dichloropalladium(II) (3.3 kg, 4.8 mol) was added and the reaction mixture was stirred at 70° C. for >1 hour. The reaction mixture was cooled to room temperature, stirred 1.5 hours at this temperature and filtered through a charcoal filter. The filter was washed with a mixture of water and acetonitrile (3:7). The filtrate was concentrated by distillation under vacuum to remove all acetonitrile. After cooling to room temperature, dichloromethane (160 l) and water (100 l) were added. The phases were stirred, separated and the organic phase was washed with water. The aqueous phases were extracted with the same portion of dichloromethane. The combined organic phases were concentrated to a volume of 60 l and the solvent was exchanged with ethanol at constant volume. The suspension obtained was cooled to −5° C., stirred at this temperature for at least one hour and filtered off. The precipitate was washed with ethanol cooled to −12 to −20° C. The solid was dried at 70° C. under vacuum affording tert-butyl 4-(6-amino-5-methyl-3-pyridyl)-3,6-dihydro-2H-pyridine-1-carboxylate (16.9 kg, 74%) as an off-white solid.

1H-NMR (600 MHz, DMSO-d6): 7.86 (s, 1H), 7.35 (s, 1H), 5.93 (sbr, 1H), 5.73 (s, 2H), 3.94 (sbr, 2H), 3.50 (sbr, 2H), 2.38 (sbr, 2H), 2.04 (s, 3H), 1.42 (s, 9H); MS(ISP): m/e=290.19 (M+H$^+$).

Example 2: tert-Butyl 4-(6-amino-5-methyl-3-pyridyl)piperidine-1-carboxylate

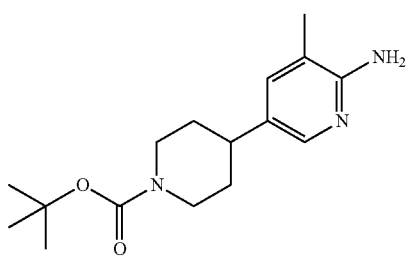 [SMILES: Cc1cc(C2CCN(C(=O)OC(C)(C)C)CC2)cnc1N]

tert-Butyl 4-(6-amino-5-methyl-3-pyridyl)-3,6-dihydro-2H-pyridine-1-carboxylate (136 g, 470.0 mmol) and the Pd-catalyst (Pd/C 10%, Noblyst P1070, E101 NE/W) (13.6 g) were suspended in THF (930 g) in an autoclave. The reaction mixture was hydrogenated at 40° C. and 11 bar (10 bar overpressure) hydrogen for 24 hours. The reaction mixture was cooled to 20° C. and filtered. The autoclave and the filter were rinsed with THF (533 g) and the filtrate was partially concentrated under normal pressure. THF (356 g) was added and the solution was concentrated again. The solution was diluted with THF (381 g) to obtain tert-butyl 4-(6-amino-5-methyl-3-pyridyl)piperidine-1-carboxylate as a ca. 17% solution in THF in quantitative yield, having a purity of 99.1%.

Example 3: 3-methyl-5-(1-methyl-4-piperidyl)pyridin-2-amine

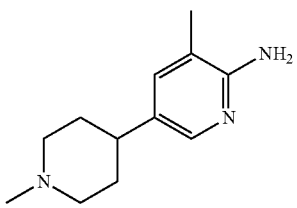

A solution of LiAlH$_4$ in THF (4.6%, 151.8 g, 180.0 mmol) was warmed to 55° C. To this solution a 10.8% solution of tert-butyl 4-(6-amino-5-methyl-3-pyridyl)piperidine-1-carboxylate in THF (243.4 g solution containing 26.2 g, 90.0 mmol tert-butyl 4-(6-amino-5-methyl-3-pyridyl)piperidine-1-carboxylate) was added at 55° C. over a period of 1 hour. The reaction mixture was stirred for 3 hours at 55° C. and then cooled to 0-5° C. A THF/water mixture (53.0 g THF and 6.8 g water) was added at 0-5° C. within 30 minutes followed by the addition of 4.2% NaOH (28.6 g) at 8-15° C. within 30 minutes. The suspension was warmed to room temperature, stirred for 30 minutes and filtered. The filter cake was washed with THF (142.2 g). The filtrate was partially concentrated in vacuo. The distillation was continued in vacuo and the volume was kept constant by simultaneous addition of heptane (114 g). The suspension was warmed to 75° C. and stirred for 10 minutes. Subsequently the reaction mixture was cooled to room temperature within 7 hours and stirred over night at room temperature. The solid was filtered, washed with heptane (24.0 g) and dried at 50° C. in vacuo to afford 3-methyl-5-(1-methyl-4-piperidyl)pyridin-2-amine (16.0 g, 86.2% yield) as a colorless solid, having a purity of 99.0%.

Example 4: ethyl 4-hydroxy-6-methyl-pyrazolo[1,5-a]pyrazine-2-carboxylate

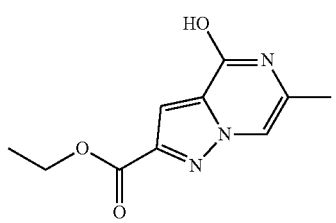 [SMILES: CCOC(=O)c1cc2c(O)nc(C)cn2n1]

1-Chloropropan-2-one (10.5 kg, 113 mol) was added slowly at room temperature (exothermic) to a suspension of diethyl 1H-pyrazole-3,5-dicarboxylate (20 kg, 94.2 mol) and cesium carbonate (30.7 kg, 94.2 mol) in acetone (200 l). The reaction mixture was stirred for 1.5 hours, filtered and the precipitate was washed with acetone. Acetone was distilled off from the filtrate at 60° C. to obtain a volume of 60-90 l, DMSO (85 l) was added and the distillation was continued until acetone was completely removed. Ammonium acetate (14.5 kg, 188 mol) was added at room temperature. The reaction mixture was stirred at 80° C. for 18 hours, cooled to 60° C. and water (290 l) was slowly added. The suspension was stirred 2 hours at 0-5° C. The precipitate was filtered off, washed with water and dried at 70° C. under high vacuum affording ethyl 4-hydroxy-6-methyl-pyrazolo[1,5-a]pyrazine-2-carboxylate (16.8 kg, 80.6%) as beige crystals.

$^1$H-NMR (600 MHz, DMSO-d6): 11.51 (s, 1H), 7.62 (s, 1H), 7.32 (s, 1H), 4.33 (q, 2H), 2.14 (s, 3H), 1.32 (t, 3H); MS(ISP): m/e=222.09 (M+H$^+$).

Example 5: ethyl 4-chloro-6-methyl-pyrazolo[1,5-a]pyrazine-2-carboxylate

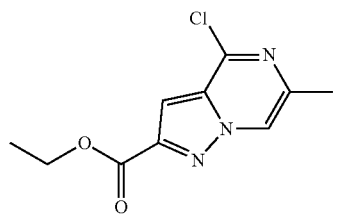

N,N-dimethyl-p-toluidine (20.5 kg, 152 mol) was added to a suspension of ethyl 4-hydroxy-6-methyl-pyrazolo[1,5-a]pyrazine-2-carboxylate (16.8 kg, 75.9 mol) in toluene (170 l) at room temperature. The reaction mixture was heated to 100° C., phosphorusoxychloride (23.3 kg, 152 mol) was added and stirring at this temperature was pursued for 22 hours. The reaction mixture was cooled to room temperature and stirred for more than an hour at rt. The precipitate was filtered off, washed with toluene and dried at 50° C. under high vacuum affording ethyl 4-chloro-6-methyl-pyrazolo[1,5-a]pyrazine-2-carboxylate (15.9 kg, 85.6%) as off-white crystals.

$^1$H-NMR (600 MHz, DMSO-d6): 8.81 (s, 1H), 7.41 (s, 1H), 7.32 (s, 1H), 4.38 (q, 2H), 2.46 (s, 3H), 1.35 (t, 3H); MS(ISP): m/e=240.05 and 242.05 (M+H$^+$).

Example 6: ethyl 4-ethyl-6-methyl-pyrazolo[1,5-a]pyrazine-2-carboxylate

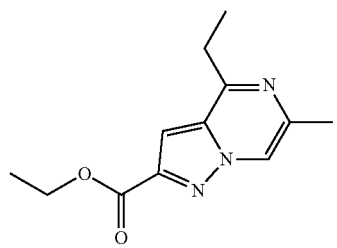 [SMILES: CCOC(=O)c1cc2c(CC)nc(C)cn2n1]

A suspension of ethyl 4-chloro-6-methyl-pyrazolo[1,5-a]pyrazine-2-carboxylate (24.0 g, 100.0 mmol), ethylboronic acid (13.3 g, 180.0 mmol) and potassium carbonate (41.5 g, 300.0 mmol) in anisole (179 g) was heated to 95° C. To the reaction mixture was added a solution of Pd(dppf)Cl$_2$ (293 mg, 0.40 mmol) in dichloromethane (34.4 g) within 45 minutes and the reaction mixture was stirred for further 30 minutes at 95-100° C. The reaction mixture was cooled to 50° C. and ethyl acetate (162 g), water (144 g) and 25% aqueous ammonium hydroxyde (6.5 g) were added to the reaction mixture at 45-50° C. The biphasic mixture was filtered via a filter loaded with Dicalite (8.5 g) and the reaction vessel and the filter cake was washed with ethyl acetate (9.0 g). The layers of the filtrate were separated at 45-50° C. The aqueous phase was removed and water (48.0 g) was added to to organic phase. The biphasic mixture was stirred for 5 minutes and the layers were separated. The aqueous phase was removed and the organic phase was partially concentrated in vacuo. The residue was diluted with ethanol (75.8 g) at 90-65° C. The solution was cooled to 0° C. within 3 hours and the resulting suspension was stirred for 30 minutes at 0° C. The solid was filtered, washed with cold ethanol (42.0 g) and dried at 20° C. in vacuo to afford ethyl 4-ethyl-6-methyl-pyrazolo[1,5-a]pyrazine-2-carboxylate (19.5 g, 83.4% yield) as pale yellow solid, having a purity of 99.8%.

Example 7: Ethyl 4-ethyl-6-methyl-pyrazolo[1,5-a]pyrazine-2-carboxylate

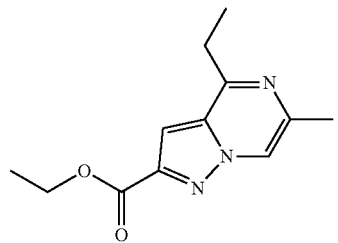 [SMILES: CCOC(=O)c1cc2c(CC)nc(C)cn2n1]

A suspension of ethyl 4-chloro-6-methyl-pyrazolo[1,5-a]pyrazine-2-carboxylate (24.0 g, 100.0 mmol), ethylboronic acid (9.61 g, 130.0 mmol), potassium carbonate (30.4 g, 220.0 mmol) and Pd(dppf)Cl$_2$ (293 mg, 0.40 mmol) in toluene (232 g) was heated to 95° C. within 2 hours and stirred at 95° C. for 3 hours. The reaction mixture was cooled to 70-80° C. and water (144 g) and 25% aqueous ammonium hydroxyde (6.5 g) were added to the reaction mixture at 80-50° C. The biphasic mixture was stirred for 30 minutes at 50° C., subsequently the layers were separated. The aqueous phase was removed and water (49.4 g) was added to to organic phase. The biphasic mixture was stirred for 20 minutes at 50° C. and filtered via a filter loaded with Dicalite (8.5 g). The reaction vessel and the filter were rinsed with toluene (30.0 g). The layers were separated and the aqueous phase was removed. The organic phase was concentrated in vacuo and the residue was diluted with ethanol (105 g) at 90-65° C. The solution was cooled to −10° C. within 7 hours and the resulting suspension was stirred for 2 hours at −10° C. The solid was filtered, washed with cold ethanol (55.2 g) and dried at 45-50° C. in vacuo to afford ethyl 4-ethyl-6-methyl-pyrazolo[1,5-a]pyrazine-2-carboxylate (21.3 g, 91.0% yield) as pale yellow solid, having a purity of 100%.

Example 8: 4-ethyl-6-methyl-pyrazolo[1,5-a]pyrazine-2-carbaldehyde

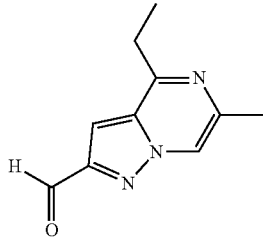

A 71% solution of Red-Al® in toluene (34.0 g, 119.6 mmol) was diluted with TBME (199 g) and cooled to −7 to −10° C. Subsequently, a solution of 1-methyl-piperazine (12.8 g, 128.0 mmol) in TBME (74.3 g) was added at −5 to −8° C. over a period of 30 minutes and the reaction mixture was warmed to 20° C.

In a second reactor ethyl 4-ethyl-6-methyl-pyrazolo[1,5-a]pyrazine-2-carboxylate (18.7 g, 80.0 mmol) was suspended in TBME (92.1 g) and the suspension was cooled to −7 to −5° C. To this suspension was added the above prepared solution of modified Red-Al® (321 g) at −5 to −8° C. within 1 hour and the reaction mixture was stirred for 5 hours at 5-7° C. If the conversion is not as desired more Red-Al® can be added. The reaction mixture was cooled to −5° C. and a cooled mixture of citric acid (87.6 g), water (78.6 g) and 28% NaOH (150.2 g) was slowly at −5 to 5° C. The biphasic mixture was warmed to 50° C. and the phases were separated. The aqueous phase was removed and a solution of citric acid (8.0 g) in water (50.0 g) was added to the organic phase. The biphasic mixture was stirred for 5 minutes at 50° C., then the phases were separated. The aqueous layer was removed and the organic phase was partially concentrated in vacuo. The distillation was continued in vacuo and the volume was kept constant by simultaneous addition of THF (178 g). The distillation was continued slowly in vacuo and the volume was kept constant by simultaneous addition of water (190 g). After the solvent exchange the suspension was cooled to 50° C. and 8% NaHCO₃ (85.0 g) was added. The suspension was cooled to 20° C. within 2 hours and stirred another hour at 20° C. The solid was filtered, washed with water (190 g) and dried at 40° C. in vacuo to afford 4-ethyl-6-methyl-pyrazolo[1,5-a]pyrazine-2-carbaldehyde (13.4 g, 88.0% yield) as a pale yellow solid, having a purity of 99.9%.

Example 9: (E)-1-(4-ethyl-6-methyl-pyrazolo[1,5-a]pyrazin-2-yl)-N-[3-methyl-5-(1-methyl-4-piperidyl)-2-pyridyl]methanimine

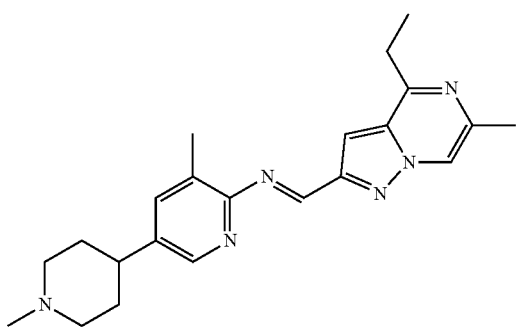

A suspension of 4-ethyl-6-methyl-pyrazolo[1,5-a]pyrazine-2-carbaldehyde (9.46 g, 50.0 mmol) and 3-methyl-5-(1-methyl-4-piperidyl)pyridin-2-amine (10.3 g, 50.0 mmol) in toluene (86.5 g) was warmed to 112° C. From the resulting solution toluene is distilled at normal pressure and the volume was kept constant by simultaneous addition of fresh toluene (86.5 g). The solution was heated under reflux for further 8 hours. Subsequently the reaction mixture was cooled to 20° C. within 2 hours and used as is for the preparation of 2-(4-ethyl-6-methyl-pyrazolo[1,5-a]pyrazin-2-yl)-9-methyl-7-(1-methyl-4-piperidyl)pyrido[1,2-a]pyrimidin-4-one.

Example 10: (E)-1-(4-ethyl-6-methyl-pyrazolo[1,5-a]pyrazin-2-yl)-N-[3-methyl-5-(1-methyl-4-piperidyl)-2-pyridyl]methanimine

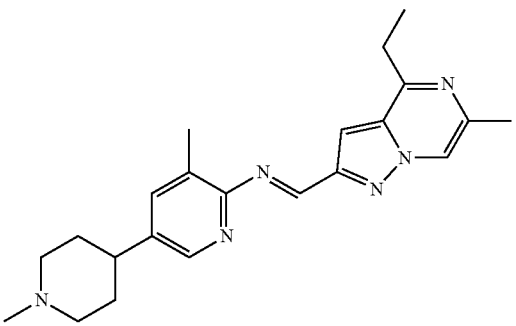

A suspension of 4-ethyl-6-methyl-pyrazolo[1,5-a]pyrazine-2-carbaldehyde (60 g, 317 mmol) and 3-methyl-5-(1-methyl-4-piperidyl)pyridin-2-amine (65.1 g, 317 mmol) in toluene (519 g) was heated to reflux. From the resulting solution the azeotropic mixture water/toluene was distilled off within 2 hours at normal pressure and the volume was kept constant by simultaneous addition of fresh toluene (104 g). The solution was heated under reflux for further 14 hours with a water trap. Subsequently the reaction mixture was evaporated under reduced pressure at 60° C. to afford (E)-1-(4-ethyl-6-methyl-pyrazolo[1,5-a]pyrazin-2-yl)-N-[3-methyl-5-(1-methyl-4-piperidyl)-2-pyridyl]methanimine (120.6 g; GC purity: 97.60%; quantitative yield)

Example 11: 2-(4-ethyl-6-methyl-pyrazolo[1,5-a]pyrazin-2-yl)-9-methyl-7-(1-methyl-4-piperidyl)pyrido[1,2-a]pyrimidin-4-one

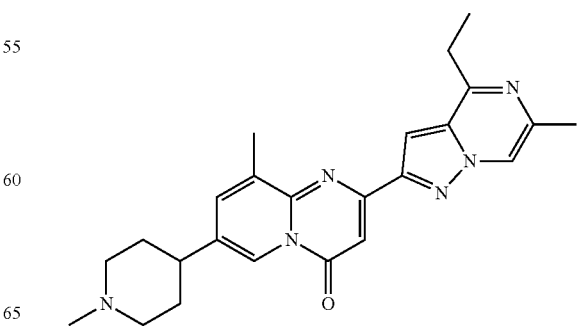

(E)-1-(4-ethyl-6-methyl-pyrazolo[1,5-a]pyrazin-2-yl)-N-[3-methyl-5-(1-methyl-4-piperidyl)-2-pyridyl]methanimine (20.0 g (53.0 mmol); obtained as described in example 10) was diluted with toluene (121 g) and cooled to −10° C. Triethylamine (76.3 g, 750 mmol) were added at −10° C. followed by the addition of a solution of methoxy acetyl chloride (11.2 g, 100 mmol) in toluene (38.9 g) at −10° C. within 1 hour. The reaction mixture was warmed to 80-85° C. within 4 hours and stirred at 80-85° C. for 3 hours. Subsequently the reaction mixture was cooled to 70-75° C. and partially concentrated in vacuo. Water (50.0 g) was added to the reaction mixture at 70-75° C. and the phases were separated. The aqueous phase was removed and water (50.0 g) was added to the organic phase at 70-75° C. The biphasic mixture was stirred for 10 minutes and the phases were separated. The aqueous phase was removed and water (50.0 g) was added to the organic phase at 70-75° C. The biphasic mixture was stirred for 10 minutes and the phases were separated at 70-75° C. The aqueous phase was removed. The organic phase was diluted with toluene (160 g) and partially concentrated in vacuo. Subsequently the reaction mixture was heated to reflux and solids on the vessel wall were dissolved. The solution was cooled to −12° C. within 5 hours. The solid was filtered, washed with toluene (69.2 g) and dried at 60° C. in vacuo to afford 2-(4-ethyl-6-methyl-pyrazolo[1,5-a]pyrazin-2-yl)-9-methyl-7-(1-methyl-4-piperidyl)pyrido[1,2-a]pyrimidin-4-one (13.6 g, 61.5% yield) as a pale yellow solid, having a purity of 100%.

Example 12: 2-(4-ethyl-6-methyl-pyrazolo[1,5-a]pyrazin-2-yl)-9-methyl-7-(1-methyl-4-piperidyl)pyrido[1,2-a]pyrimidin-4-one

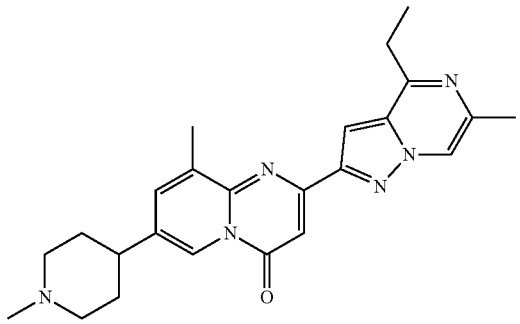

A solution of crude (E)-1-(4-ethyl-6-methyl-pyrazolo[1,5-a]pyrazin-2-yl)-N-[3-methyl-5-(1-methyl-4-piperidyl)-2-pyridyl]methanimine (59.5 g, 158 mmol) and di-isopropyl-ethylamine (68.6 g, 531 mmol) in dichloromethane (576 g) was added into a dry reaction vessel containing zinc chloride (4.31 g, 31.6 mmol). The yellow suspension was cooled to 0-5° C. and a solution of chloroacetyl chloride (30 g, 265 mmol) in dichloromethane (133 g) was added within 50 minutes. After 3 hours stirring at room temperature, di-isopropyl-ethylamine (6.94 g, 53.7 mmol) and chloroacetyl chloride (3.03 g, 26.9 mmol) were added in that row at room temperature. After a further 30 minutes stirring, di-isopropyl-ethylamine (6.94 g, 53.7 mmol) and chloroacetyl chloride (3.03 g, 26.9 mmol) were added again in that row at room temperature. After a further 30 minutes stirring, the reaction mixture was poured onto aqueous HCl 0.5M (957 mL, 478 mmol), dichloromethane (479 g) was added and the pH of the aqueous phase was brought to 1-1.5 by the addition of 25% aqueous HCl (22.4 g, 154 mmol). After vigorous stirring, the phases were separated. The aqueous phase was washed with two portions of dichloromethane (197 g each). Toluene (1.03 kg) and water (89.7 g) were added to the aqueous phase. The pH was brought to =>12 by addition of 28% aqueous sodium hydroxide (ca. 250 mL) under vigorous stirring within 30 minutes. The biphasic mixture was heated to 65° C., whereby most solids were dissolved. The phases were separated and the organic phase was washed with two portions of water (598 g each) at 65° C. The organic phase was diluted with toluene (259 g) and residual dichloromethane and water were distilled off at 60-70° C. under reduced pressure. Subsequently active charcoal (3.29 g) was added, the suspension was stirred 15 minutes at 65° C. and filtered at this temperature. The filtrate was concentrated to a volume of 550 mL at 60-70° C. under reduced pressure. The suspension was heated to 98° C., then cooled to −5-0° C. within 16 hours and stirred a further 3 hours at this temperature. The precipitate was filtered off, washed with cold toluene (69.2 g) and dried at 5° C. in vacuum to afford 2-(4-ethyl-6-methyl-pyrazolo[1,5-a]pyrazin-2-yl)-9-methyl-7-(1-methyl-4-piperidyl)pyrido[1,2-a]pyrimidin-4-one (52.3 g, HPLC purity: 99.4%, 79.4% yield) as a light beige solid.

Example 13: 2-(4-ethyl-6-methyl-pyrazolo[1,5-a]pyrazin-2-yl)-9-methyl-7-(1-methyl-4-piperidyl)pyrido[1,2-a]pyrimidin-4-one

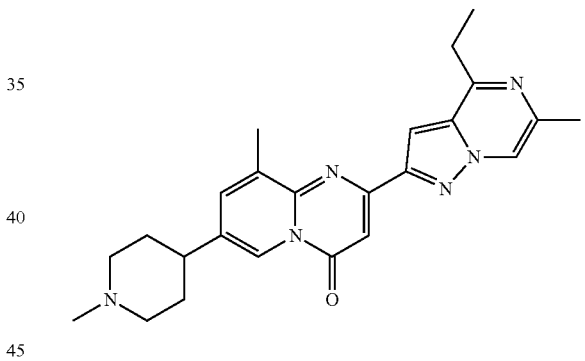

To a reaction mixture of crude (E)-1-(4-ethyl-6-methyl-pyrazolo[1,5-a]pyrazin-2-yl)-N-[3-methyl-5-(1-methyl-4-piperidyl)-2-pyridyl]methanimine (4.41 g, 11.7 mmol), di-isopropyl-ethylamine (4.33 g, 32.8 mmol) and zinc chloride (319 mg, 2.34 mmol) in dichloromethane (58.4 g) was added at 0° C. a solution of chloroacetyl chloride (1.85 g, 16.4 mmol) in dichloromethane (23.4 g) within 10 minutes. After 1.5 hours stirring at room temperature, the reaction mixture was poured onto water (200 mL), the pH was adjusted to 1 by addition of aqueous HCl 1M (42.3 g, 35.3 mmol) and the aqueous phase was extracted with dichloromethane (150 mL). The pH of the aqueous phase was brought to 14 by the addition of 32% aqueous sodium hydroxide (9.45 g, 75.6 mmol). The aqueous phase was extracted with two portions of dichloromethane (100 mL, each). The combined organic layers were dried, evaporated and dried under high vacuum to give 4.71 g of a yellow solid. This solid was crystallized from n-propanol (22.1 mL) and n-propyl acetate (17.6 mL) to afford 2-(4-ethyl-6-methyl-pyrazolo[1,5-a]pyrazin-2-yl)-9-methyl-7-(1-methyl-4-piperidyl)pyrido[1,2-a]pyrimidin-4-one (3.15 g, HPLC purity: 98.6%, 64.6% yield) as off-white crystals.

Example 14a: Preparation of Crystalline Form a (Spontaneous Crystallization)

2-(4-Ethyl-6-methylpyrazolo[1,5-a]pyrazin-2-yl)-9-methyl-7-(1-methylpiperidin-4-yl)-4H-pyrido[1,2-a]pyrimidin-4-one (1.0 g, 2.4 mmol; assay 98.5%-m/m) was dissolved in a mixture of Ethanol/water 80/20 m/m (12.5 g) upon heating to complete dissolution. The clear polish-filtered solution was cooled to ambient temperature by natural cooling upon which spontaneous crystallization occurred The solid was isolated by filtration and dried at 60° C. under vacuum for 16 h affording 0.75 g of Form A (75% yield).

Example 14b: Preparation of Crystalline Form a (Spontaneous Crystallization)

2-(4-Ethyl-6-methylpyrazolo[1,5-a]pyrazin-2-yl)-9-methyl-7-(1-methylpiperidin-4-yl)-4H-pyrido[1,2-a]pyrimidin-4-one (103.5 g, 248 mmol) was dissolved in 1-Propanol (560 g) and n-Propyl acetate (463 g) upon heating to reflux. The clear orange to red colored solution was cooled to 60° C. internal temperature upon which spontaneous crystallization occurred at approx. 82° C. internal temperature. The suspension was stirred at 60° C. for 1 h, cooling to ambient temperature and stirred over night at ambient temperature. The suspension was filtered and washed with a mixture of 1-Propanol (40.0 g) and n-Propyl acetate (89.0 g). The filter cake was dried at 60° C. under vacuum affording 89.2 g of Form A as orange crystals (86% yield).

Example 15: Preparation of Crystalline Form F (Spontaneous Crystallization)

2-(4-Ethyl-6-methylpyrazolo[1,5-a]pyrazin-2-yl)-9-methyl-7-(1-methylpiperidin-4-yl)-4H-pyrido[1,2-a]pyrimidin-4-one (0.05 g; 0.1 mmol; assay approx. 98.7%-m/m, purity approx. 99.7%-a/a) was dissolved in Toluene (0.4-0.7 mL) upon heating to above 80° C. The solution was cooled to 5° C. while spontaneous crystallization occurred. The suspension was filtered and the wet cake dried at 22° C. under vacuum overnight affording Form F.

Example 16: Preparation of Crystalline Form F (Seeded)

2-(4-Ethyl-6-methylpyrazolo[1,5-a]pyrazin-2-yl)-9-methyl-7-(1-methylpiperidin-4-yl)-4H-pyrido[1,2-a]pyrimidin-4-one (20 g; 48.0 mmol) was dissolved in 1-Butanol/water 98:2 m/m (180 g) upon heating to internal temperature of 85° C. The clear yellowish solution was cooled to internal temperature of 75° C. followed by addition of a suspension of 2-(4-Ethyl-6-methylpyrazolo[1,5-a]pyrazin-2-yl)-9-methyl-7-(1-methylpiperidin-4-yl)-4H-pyrido[1,2-a]pyrimidin-4-one Form F seeding crystals (0.4 g; 1.0 mmol) suspended in 1-Butanol/water 98:2 m/m (2 g). The suspension was stirred for additional 30 min at 75° C. internal temperature followed by cooling to 0° C. with a cooling rate of 0.1° C./min. At 0° C. internal temperature the suspension was stirred for another 5 hours prior to filtration. After filtration the wet cake was rinsed with 1-Butanol/water 98:2 m/m (20 g) and dried at 50° C. under vacuum for 3 days affording 17.68 g of Form F with a purity of 99.9% (HPLC) (yield: 88%).

The invention claimed is:

1. A process for the preparation of compound of formula (I):

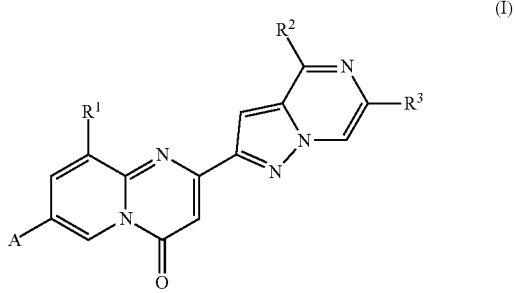

which comprises reacting compound of formula (II):

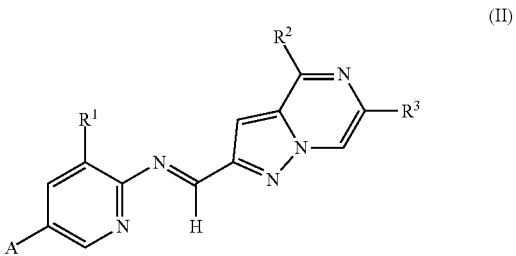

with a compound of formula (III):

wherein $R^1$ is hydrogen, $C_{1-7}$-alkyl, or $C_{3-8}$-cycloalkyl;

$R^2$ is hydrogen, halo, $C_{1-7}$-alkyl, $C_{1-7}$-haloalkyl or $C_{3-8}$-cycloalkyl;

$R^3$ is hydrogen or $C_{1-7}$-alkyl;

$R^4$ is $C_{1-7}$-alkoxy;

A is

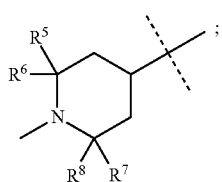

$R^5$ to $R^8$ are each independently selected from hydrogen and $C_{1-3}$-alkyl.

2. A process according to claim 1, which further comprises the preparation of the compound of formula (II):

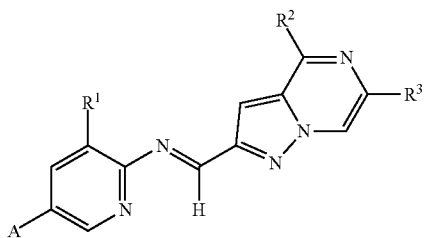

(II)

which comprises reacting compound of formula (IV)

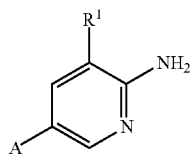

(IV)

with a compound of formula (V)

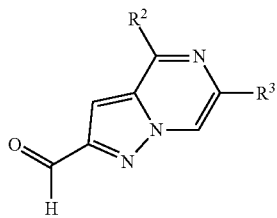

(V)

wherein,
$R^1$ is hydrogen, $C_{1-7}$-alkyl, or $C_{3-8}$-cycloalkyl;
$R^2$ is hydrogen, halo, $C_{1-7}$-alkyl, $C_{1-7}$-haloalkyl or $C_{3-8}$-cycloalkyl;
$R^3$ is hydrogen or $C_{1-7}$-alkyl;
A is

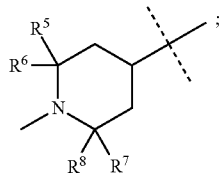

$R^5$ to $R^8$ are each independently selected from hydrogen and $C_{1-3}$-alkyl.

3. A process according to claim 2, which further comprises the preparation of the compound of formula (V):

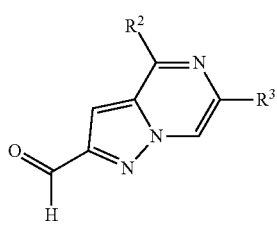

(V)

which comprises reacting a compound of formula (VII)

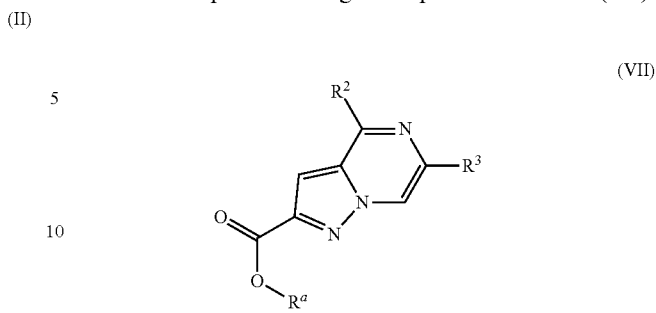

(VII)

wherein
$R^2$ is hydrogen, halo, $C_{1-7}$-alkyl, $C_{1-7}$-haloalkyl or $C_{3-8}$-cycloalkyl;
$R^3$ is hydrogen or $C_{1-7}$-alkyl;
with a reducing agent.

4. A compound of formula (II):

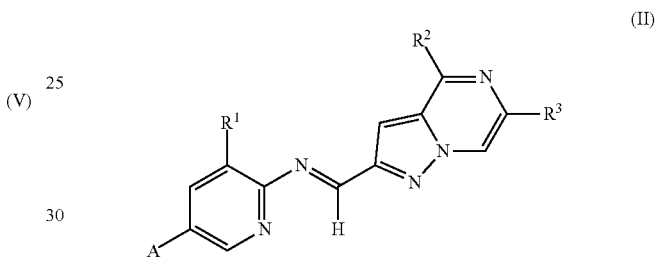

(II)

wherein,
$R^1$ is hydrogen, $C_{1-7}$-alkyl, or $C_{3-8}$-cycloalkyl;
$R^2$ is hydrogen, halo, $C_{1-7}$-alkyl, $C_{1-7}$-haloalkyl or $C_{3-8}$-cycloalkyl;
$R^3$ is hydrogen or $C_{1-7}$-alkyl;
A is

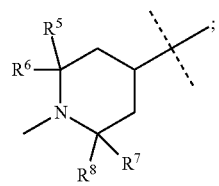

$R^5$ to $R^8$ are each independently selected from hydrogen and $C_{1-3}$-alkyl.

5. A compound of formula (V):

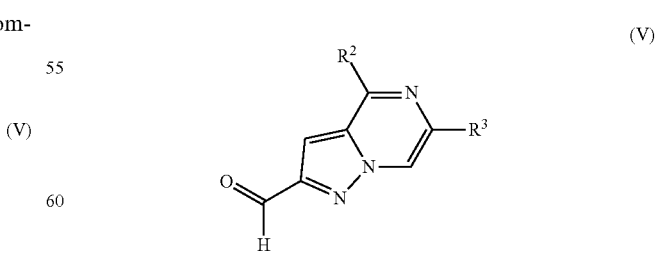

(V)

wherein
$R^2$ is hydrogen, halo, $C_{1-7}$-alkyl, $C_{1-7}$-haloalkyl or $C_{3-8}$-cycloalkyl;
$R^3$ is hydrogen or $C_{1-7}$-alkyl.

6. A process according to claim 1, wherein $R^4$ is methoxy.

7. A process according to claim 3, wherein the reducing agent is a hindered organoborane, an organo-aluminium hydride or inorgano-aluminium hydride.

8. A process according to claim 3, wherein the reducing agent is sodium bis-(2-methoxyethoxy)aluminium hydride.

9. A process according to claim 1, wherein $R^1$ is methyl.

10. A process according to claim 1, wherein $R^2$ is ethyl.

11. A process according to claim 1, wherein $R^3$ is methyl.

12. A process according to claim 1, wherein A is

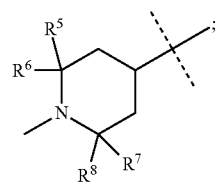

$R^5$, $R^6$, $R^7$ and $R^8$ are hydrogen.

13. A compound of formula (II'):

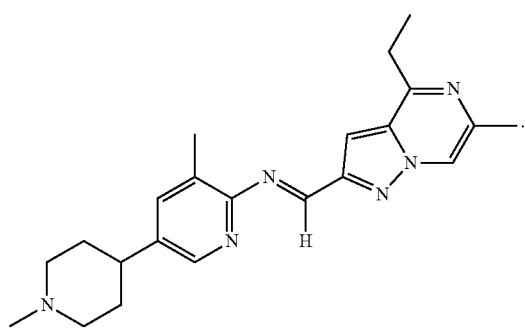

(II')

14. A compound of formula (IV'):

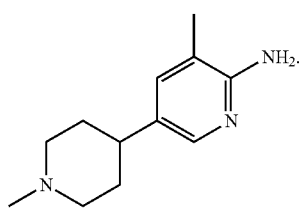

(IV')

15. A compound of claim 5 of formula (V')

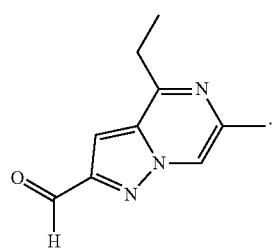

(V')

16. A solid form of a compound of formula (I') or a salt thereof

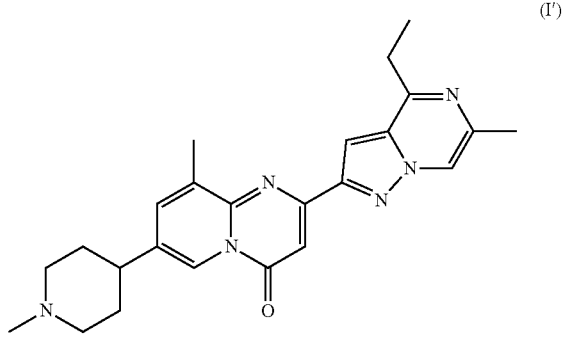

(I')

characterized by an XRPD diffraction pattern comprising an XRPD peak at an angle of diffraction 2Theta at about 10.3°, 12.3°, 13.3°, and 15.4° (±0.2°).

17. The solid form according to claim 16, characterized by the XRPD diffraction pattern comprising XRPD peaks at angles of diffraction 2Theta at about 8.5°, 10.3°, 12.3°, 13.3°, 15.4°, 17.7°, 18.1°, 19.1°, 19.6°, 19.9°, 21.1°, 21.3°, 21.5°, 22.8°, 24.0° and 25.0°.

18. A solid form of a compound of formula (I') or a salt thereof

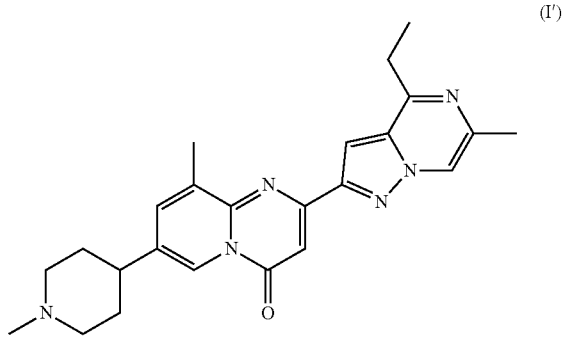

(I')

characterized by an XRPD diffraction pattern comprising an XRPD peak at an angle of diffraction 2Theta at about 8.0°, 9.1°, 15.0°, and 23.7° (±0.2°).

19. The solid form according to claim 17, characterized by the XRPD diffraction pattern comprising XRPD peaks at angles of diffraction 2Theta at about 8.0°, 8.3°, 9.1°, 11.7°, 12.5°, 13.5°, 14.7°, 15.0°, 15.4°, 16.0°, 16.1°, 16.6°, 17.0°, 19.3°, 20.6°, 21.0°, 21.5° 23.0°, 23.1°, 23.6°, 23.7°, 23.9°, 27.0°, 27.3° and 28.3°.

* * * * *